United States Patent [19]
Skotheim et al.

[11] Patent Number: 5,264,092
[45] Date of Patent: Nov. 23, 1993

[54] REDOX POLYMER MODIFIED ELECTRODE FOR THE ELECTROCHEMICAL REGENERATION OF COENZYME

[75] Inventors: Terje Skotheim, Shoreham, N.Y.; Yoshiyuki Okamoto, Fort Lee, N.J.; Lo G. Gorton, Malmo, Sweden; Hung Sui Lee, East Setauket; Paul Hale, East Northport, both, N.Y.

[73] Assignee: Moltech Corporation, Stony Brook, N.Y.

[21] Appl. No.: 770,310

[22] Filed: Oct. 2, 1991

[51] Int. Cl.$^5$ .............................. G01N 27/00
[52] U.S. Cl. .................. 204/153.12; 204/403; 204/290 R; 435/817; 427/77; 429/43; 429/13
[58] Field of Search ............ 204/403, 290 R, 291, 204/294, 153.12, 131; 435/817; 427/77, 407.1, 409, 414; 429/43, 13

[56] References Cited

U.S. PATENT DOCUMENTS
4,490,464 12/1984 Gorton ...................... 204/403
4,797,181 1/1989 Durfor et al. .................. 435/817

OTHER PUBLICATIONS
Gorton, "Chemically Modified Electrodes for the Electrocatalytic Oxidation of Nicotinamide Coenzymes", J. Chem. Soc., Faraday Trans, Jan. 1986, 82 1245-1258.
Tse et al., "Electrocatalysis of Dihydronicotinamide Adenosine Diphosphate to Nh Quinons and Modified Quinone Electrodes", Amer-Chem. Soc., 1978.

Primary Examiner—Kathryn Gorgos
Attorney, Agent, or Firm—Roland Plottel

[57] ABSTRACT

The present invention relates to an electrochemical enzyme biosensor for use in liquid mixtures of components for detecting the presence of, or measuring the amount of, one or more selected components. The enzyme electrode of the present invention includes a redox polymer immobilized on an electrode surface, one or more enzymes, at least one of which is a dehydrogenase, a coenzyme and an electron collector.

9 Claims, 13 Drawing Sheets $R = +CH_2 +_x$ or $+CH_2CH_2O+_x$ ($x = 2 - 10$)

M = attached mediator molecule

M = attached mediator molecule

M = attached mediator molecule

FIG. II

REDOX POLYMER MODIFIED ELECTRODE FOR THE ELECTROCHEMICAL REGENERATION OF COENZYME

THE FIELD OF THE INVENTION

The present invention relates to an electrode modified with an electrochemically active polymer, which may be used for the oxidation of the coenzymes nicotinamide adenine dinucleotide (NADH/NAD+) and nicotinamide adenine dinucleotide phosphate (NADPH/NADP+), or analogs thereof. The polymer contains covalently attached mediator molecules which catalytically oxidize the coenzyme, and electrodes modified with this polymer can thus regenerate the oxidized form of the coenzyme with far greater ease than can unmodified electrodes. Said electrodes can be used for the electrochemical regeneration of coenzyme in biotechnical, microbiological or biochemical processes, for analysis in systems using coenzyme-dependent enzymes, or as an anode in biochemical fuel cells.

BACKGROUND OF THE INVENTION

Dehydrogenases dependent upon NAD and NADP coenzymes constitute the largest group of redox enzymes known. These enzymes catalyze reactions of the type

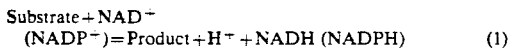

$$\text{Substrate} + \text{NAD}^+ (\text{NADP}^+) = \text{Product} + \text{H}^+ + \text{NADH (NADPH)} \quad (1)$$

These enzymes have been used in only a few amperometric biosensors, partly due to the fact that the electrochemistry of both the oxidized (NAD+) and reduced (NADH) forms of the coenzyme is very irreversible. The oxidation of NADH results in electrode fouling, while the reduction of NAD is complicated by radical formation and dimerization.

The high overvoltage of approximately 1V (J. Moiroux and P. J. Elving, Analytical Chemistry, Vol. 50, p. 1056 (1978)) required for direct oxidation of NADH brings about several important disadvantages. Because the electrode is highly oxidizing, substrates, products, enzymes, and other components in the test solution can react in an unacceptable manner. For example, reaction products may polymerize at the electrode, resulting in a deactivated surface.

The high overvoltage can be reduced to a large extent by immobilizing mediating structures onto the electrode surface (B. Persson and L. Gorton, Journal of Electroanalytical Chemistry, Vol. 292, p. 115 (1990)). The mediating reactions are generally of the type shown below:

$$\text{NADH (NADPH)} + \text{Med}^+ \rightarrow \text{NAD}^+ (\text{NADP}^+) + \text{MedH} \quad (2)$$

$$\text{MedH} \rightarrow \text{Med}^+ + \text{H}^+ + 2e \quad (3)$$

In these expressions, Med and MedH refer to the oxidized and reduced forms of the mediator, respectively. To date, all of the effective mediators are based on low molecular weight materials which are at least partially soluble in water. This limits the useful lifetime of an electrode modified with these mediators, as the mediators are free to diffuse away from the electrode surface into solution.

PRIOR ART

D. C. S. Tse and T. Kuwana (Analytical Chemistry, Vol. 50, p. 1315 (1978)) oxidized graphite electrodes in an oxygen plasma and reduced the oxygen functionalities into OH-groups with LiAlH$_4$, to which 3,4-dihydroxybenzylamine was then coupled by trichlorotriazine. The modified electrodes were capable of oxidizing NADH at a lower anodic potential (approximately +0.5V vs. the NHE) than unmodified graphite electrodes. The modified electrodes had short lifetimes (only a few operating cycles), however, and the surface covering (i.e., the number of mediating groups per unit area) was low, resulting in a very low current density.

C. Degrand and L. L. Miller (Journal of the American Chemical Society, Vol. 102, p. 5728 (1980)) made a mediating material comprised of dopamine copolymerized with poly(methacryloyl chloride). Electrodes modified with this material displayed somewhat higher lifetimes (approximately ten operating cycles). Also, the electrode potential for reoxidation of the mediator was lowered by 50 mV compared with that achieved by Tse and Kuwana. The total overvoltage for NADH oxidation was slightly below 0.8V, and the surface covering was improved.

Gorton et al. (U.S. Pat. No. 4,490,464) constructed electrodes modified with monomeric mediators such as alkyl phenazinium ions, phenazinium ions, phenoxazinium ions, phenoxazones, phenothiazinium ions, or phenothiazinones. Graphite and carbon electrodes were modified with these mediators by adsorption. The most effective mediators are those which contain the charged paraphenylenediamine structure within each molecule (B. Persson and L. Gorton, Journal of Electroanalytical Chemistry, Vol. 292, p. 115 (1990)). Substantial decreases in the overvoltage for NADH oxidation have been attained using these mediators. This decrease in overvoltage is dictated mainly by the formal potential of the mediators, which is typically in the range of −100 to −600 mV vs. SCE. The optimal voltage for sensor applications is generally −100 to +100 mV vs. SCE (L. Gorton, Journal of the Chemical Society, Faraday Transactions 1, vol. 82, p. 1245 (1986)), so the decrease in overvoltage for NADH oxidation should be approximately 450 to 600 mV. This is achieved by using mediators containing the charged paraphenylenediamine structure.

The lifetimes of electrodes modified with these adsorbed monomeric mediators is limited by their solubility in water, which allows the adsorbed species to dissolve into solution and away from the electrode surface. Improved adsorption stability has been achieved by the addition of aromatic rings to the mediator molecule (L. Gorton, Journal of the Chemical Society, Faraday Transactions 1, vol. 82, p. 1245 (1986)), yet in all cases the monomeric mediators eventually desorb from the electrode surface.

GENERAL DESCRIPTION OF THE INVENTION

The present invention comprises electrodes modified with water-insoluble redox polymers in such a manner that the electrochemical oxidation of NADH, NADPH, NADH analogs, or NADPH analogs is catalyzed. The polymers are comprised of poly(siloxane) (FIG. 1), poly(alkane) (FIG. 2), poly(ethylene oxide) (FIG. 3), or copolymers thereof, which contain covalently attached mediator molecules. The polymers can also be comprised of other polymer backbones, such as poly(ethylene imine) and poly(vinylpyridine), of polymers with cationic backbones, and of polymer backbones with covalently attached cationic side groups. The attached mediator molecules are phenazinium ions (FIG. 4, $X=N$, $Y=NR_2^+$, where R is an alkyl group), phenazinones (FIG. 4, $X=N$, $Y=O$), phenoxazinium ions (FIG. 4, $X=O$, $Y=NR_2^+$), phenoxazones (FIG. 4, $X=O$, $Y=O$), phenothiazinium ions (FIG. 4, $X=S$, $Y=NR_2^+$), phenothiazinones (FIG. 4, $X=S$, $Y=O$), or derivatives thereof.

These redox polymer-modified electrodes can be used for the electrochemical regeneration of coenzyme in biotechnical, microbiological or biochemical processes, for analysis in systems using coenzyme-dependent enzymes, or as an anode in biochemical fuel cells.

BRIEF DESCRIPTION OF THE DRAWINGS

The invention will be further described with reference to the accompanying drawings, in which.

DETAILED DESCRIPTION OF THE INVENTION

The present invention is based upon the discovery that polymeric compounds containing many covalently attached mediators can be coated onto an electrode surface in such a manner that rapid electron transfer is achieved. This immobilization method is basically different from the prior art techniques (Gorton et al., U.S. Pat. No. 4,490,464), which involved the adsorption of monomeric mediators to carbon surfaces. The present invention permits the permanent attachment of the mediators to any electrode material by coating with a water-insoluble redox polymer.

The present invention covers a class of redox polymers which has exceptional properties for mediating enzyme-catalyzed reactions in electrode sensing systems. The redox polymer acts as an insoluble catalytic layer which oxidizes the coenzyme molecules. The present system is applicable to the nicotinamide adenine dinucleotide or nicotinamide adenine dinucleotide phosphate coenzymes, or analogs thereof.

One object of the invention is to provide a redox polymer-modified electrode which is capable of regenerating the oxidized form of the above coenzymes at much lower applied potentials than occurs at unmodified electrode surfaces.

Another object of the invention is to provide an enzyme electrode for use in liquid mixtures of components for detecting the presence of, measuring the amount of and/or monitoring the level of one or more selected components capable of undergoing an enzyme-catalyzed reaction, in which a dehydrogenase enzyme, a coenzyme, and an insoluble polymeric mediator system are maintained in an immobilized state on at least an external surface of the electron collector.

Another object of the invention is to provide highly stable anodes for biochemical fuel cells. The design and construction of such a fuel cell has been reported in the literature (B. Persson et al., Bioelectrochemistry and Bioenergetics, Vol. 16, p. 479 (1986)).

Preferred polymer backbones are alkane polymers, siloxane polymers, ethylene oxide polymers, and copolymers thereof. Other preferred polymers poly(ethylene imine) and poly(vinylpyridine), polymers with cationic backbones, and polymer backbones with covalently attached cationic side groups.

Figure 1:
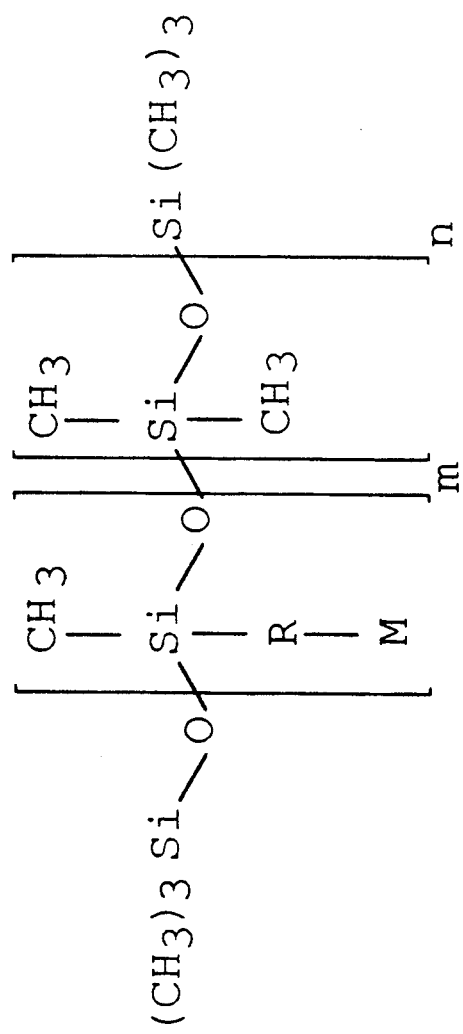
FIG. 1 illustrates the structure of the mediator-modified poly(siloxane) system.
Figure 2:
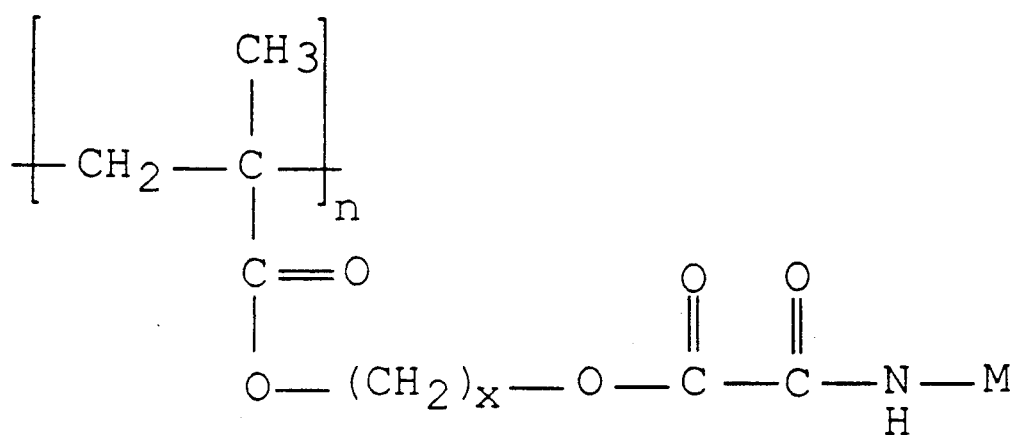
FIG. 2 illustrates the structure of the mediator-modified poly(alkane) system.
Figure 3:
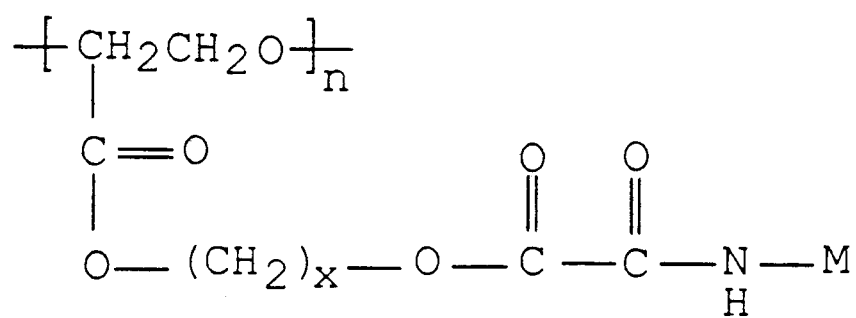
FIG. 3 illustrates the structure of the mediator-modified poly(ethylene oxide) system.
Figure 4:
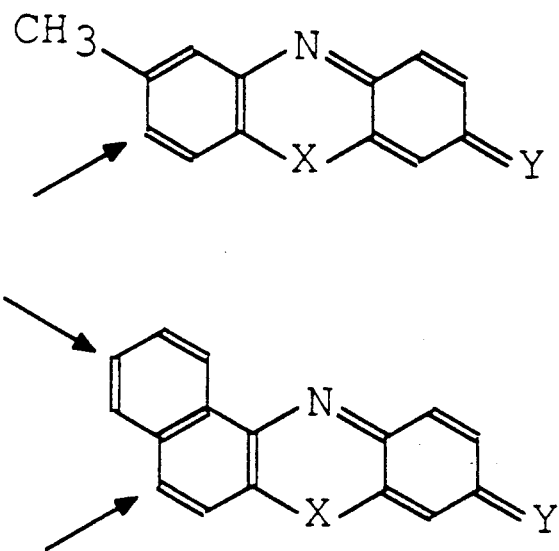
FIG. 4 illustrates the basic structure of phenazinium ions ($X=N$, $Y=NR_2^+$), phenazinones ($X=N$, $Y=O$), phenoxazinium ions ($X=O$, $Y=NR_2^+$), phenoxazones ($X=O$, $Y=O$), phenothiazinium ions ($X=S$, $Y=NR_2^+$), phenothiazinones ($X=S$, $Y=O$). The arrows indicate the preferred locations for covalent attachment to polymers, although other attachment points are not excluded.

Preferred mediator compounds are the phenazinium ions (FIG. 4, $X=N$, $Y=NR_2^+$, where R is an alkyl group), phenazinones (FIG. 4, $X=N$, $Y=O$), phenoxazinium ions (FIG. 4, $X=O$, $Y=NR_2^+$), phenoxazones (FIG. 4, $X=O$, $Y=O$), phenothiazinium ions (FIG. 4, $X=S$, $Y=NR_2^+$), phenothiazinones (FIG. 4, $X=S$, $Y=O$), or derivatives thereof.

Figure 5:
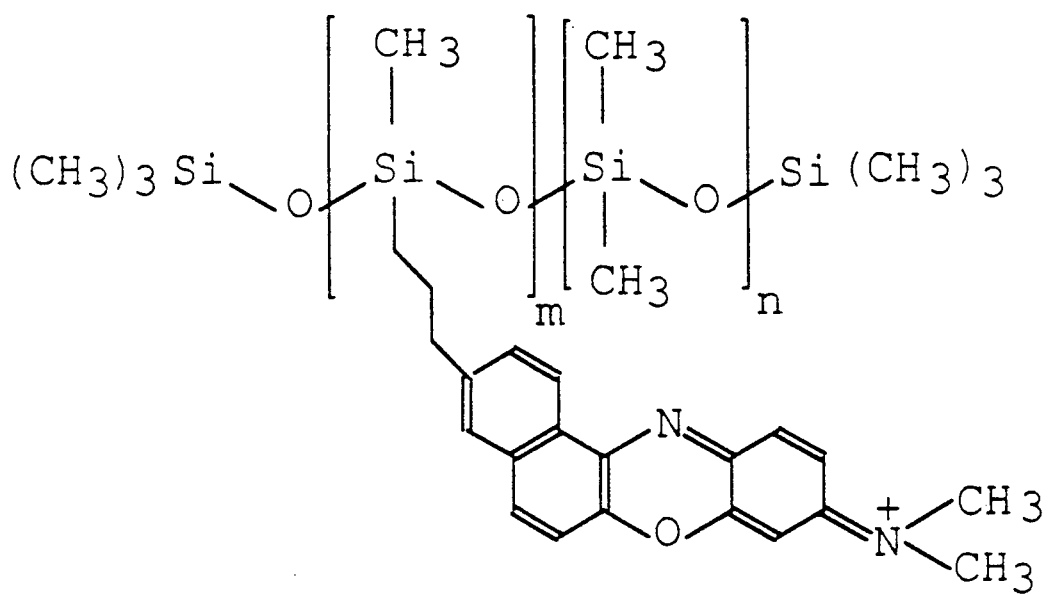
FIG. 5 illustrates the basic structure of a poly(siloxane) containing covalently attached Meldola Blue. The copolymer ratio (m:n) is approximately 1:5.

A preferred polymeric mediator system is based on a siloxane polymer backbone and attached Meldola Blue (FIG. 5). In this polymer, the m:n ratio is approximately 1:5, and the subunits are randomly distributed to form a random block copolymer.

Figure 10:
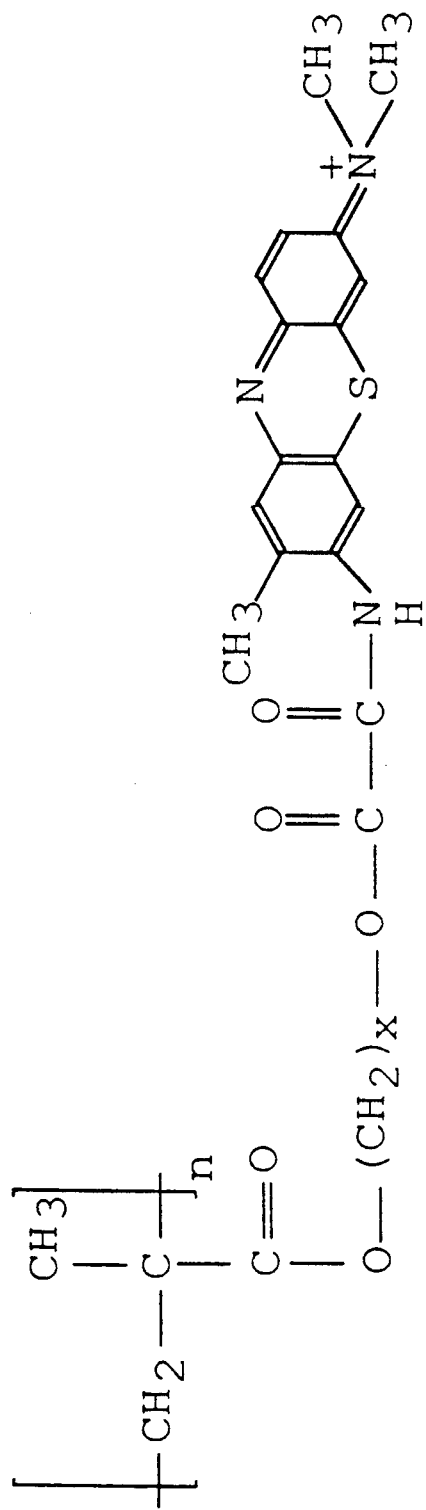
FIG. 10 illustrates the basic structure of a poly(alkane) containing covalently attached Toluidine Blue O.

A preferred polymeric mediator system is based on an alkane polymer backbone and attached Toluidine Blue O (FIG. 10).

The preferred enzymes are the NAD dependent dehydrogenases, such as alcohol dehydrogenase and glucose dehydrogenase.

The enzyme electrodes may be constructed by mixing graphite powder, the mediator-containing polymer, the coenzyme, and the enzyme and blending the resulting mixture into a paste which is subsequently packed into a well at the base of an electrode housing, as shown schematically in FIG. 13.

In order to achieve long-term stability, it is advantageous to covalently immobilize the enzyme to the polymer backbone. This can be achieved with the method described in Biosensors, Vol. 3, p. 45 (1987/88), with amine groups selectively attached to the polymer backbone on some of the polymer chains or alternately with the mediators on the same polymer chain.

In order to achieve increased stability, it is also advantageous to immobilize the cofactor molecules, nicotinamide adenine dinucleotide or nicotinamide adenine dinucleotide phosphate, to the electrode surface, to the polymer chain, or to the enzyme molecules.

A preferred electron collector material is graphite paste due to the ease of fabrication and the large surface area. Other electrode materials may be silver, platinum, nickel, aluminum, gold, glassy carbon, spectrographic graphite, pyrolytic carbon, or tin-oxide.

The manner in which the redox polymer modified electrodes and the amperometric biosensors of the present invention are constructed can be understood more fully by reference to the following illustrative examples.

EXAMPLE 1

Graphite electrode modified with Meldola Blue poly(siloxane)

Figure 6:
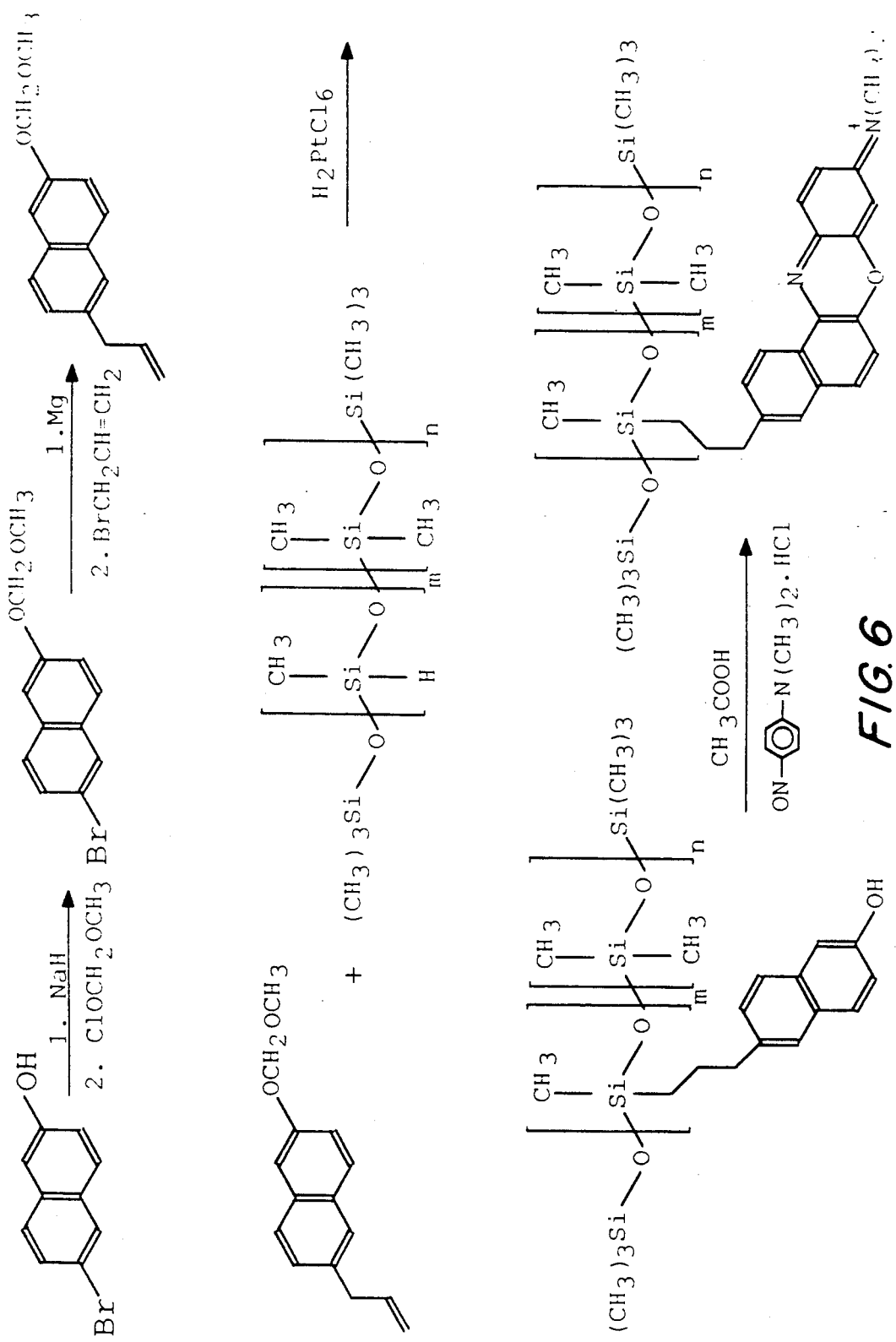
FIG. 6 illustrates the reaction sequence for the synthesis of the Meldola Blue-modified poly(siloxane) shown in FIG. 5.

The Meldola Blue containing poly(siloxane) (FIG. 5) was prepared by following the reaction sequence outlined in FIG. 6.

A solution of this redox polymer (1.1 mg/ml) was made using acetone as the solvent. An amount of 5 μl of this solution was placed onto the surface of a clean, polished spectrographic graphite electrode (electrode diameter: 3.05 mm), and the solvent was allowed to evaporate completely. The resulting polymer-modified electrode was connected to a potentiostat and cyclic voltammetry experiments, as described in the book "Electrochemical Methods—Fundamentals and Applications" by A. J. Bard and L. R. Faulkner (J. Wiley & Sons, 1980), were performed. For these measurements, the reference electrode was a saturated calomel electrode (SCE) and the auxiliary electrode consisted of a platinum wire. The experiments were conducted in 0.1M phosphate buffer solution, pH 7.0, at a sweep rate of 10 mV/s.

Figure 7:
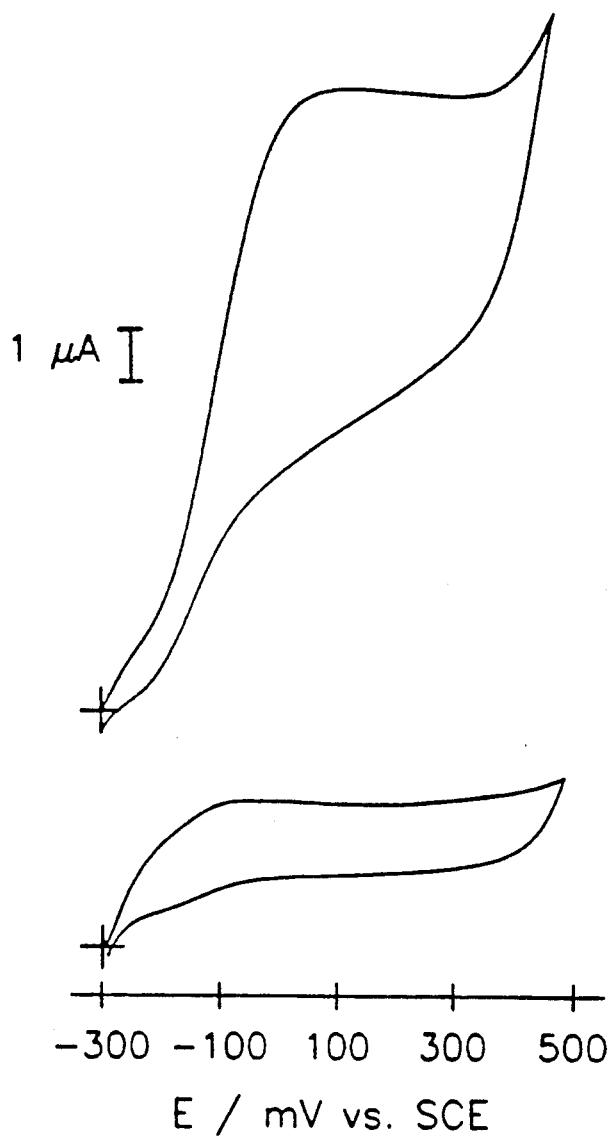
FIG. 7 illustrates cyclic voltammograms with a graphite electrode modified with the Meldola Blue modified poly(siloxane) (FIG. 5). Voltammogram (a) was measured without NADH in solution, while (b) was measured in the presence of 4 mM NADH. The experiments were conducted in 0.1M phosphate buffer solution, pH 7.0, at a sweep rate of 10 mV/s.

FIG. 7 shows the resulting cyclic voltammograms measured with the graphite electrode modified with the Meldola Blue modified poly(siloxane). Voltammogram (a) was measured without NADH in solution, and it shows small oxidation and reduction waves corresponding to the electrochemistry of the attached Meldola Blue molecules. The formal potential, taken as the average of the oxidation and reduction peak potentials, is approximately −150 to −175 mV vs. SCE, which agrees well with that measured for the monomeric Meldola Blue species (B. Persson and L. Gorton, Journal of Electroanalytical Chemistry, Vol. 292, p. 115 (1990)).

Voltammogram (b) in FIG. 7 was measured in the presence of 4 mM NADH. Compared with voltammogram (a), the anodic (oxidation) wave is increased and the cathodic (reduction) wave is decreased. This change in voltammetric response is due to the fact that when NADH from the contacting buffer reaches the electrode surface, it will react with the oxidized form of the polymer-bound Meldola Blue ($MB^+$). A complex will be formed which will rapidly decompose into $NAD^+$ and the reduced form of the mediator, MBH. The reduced form of the mediator will be electrochemically reoxidized if the applied potential is more positive than the formal potential of the $MB^+/MBH$ couple (L. Gorton et al., Journal of Electroanalytical Chemistry, Vol. 161, p. 103 (1984)). The electrochemical reactions involved are shown below.

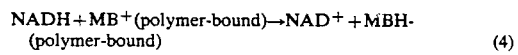

$$NADH + MB^+(\text{polymer-bound}) \rightarrow NAD^+ + MBH\text{-}(\text{polymer-bound}) \quad (4)$$

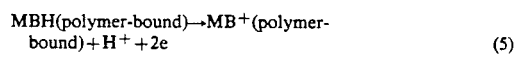

$$MBH(\text{polymer-bound}) \rightarrow MB^+(\text{polymer-bound}) + H^+ + 2e \quad (5)$$

The cyclic voltammograms clearly show the mediating ability of the Meldola Blue-containing poly(siloxane).

Figure 8:
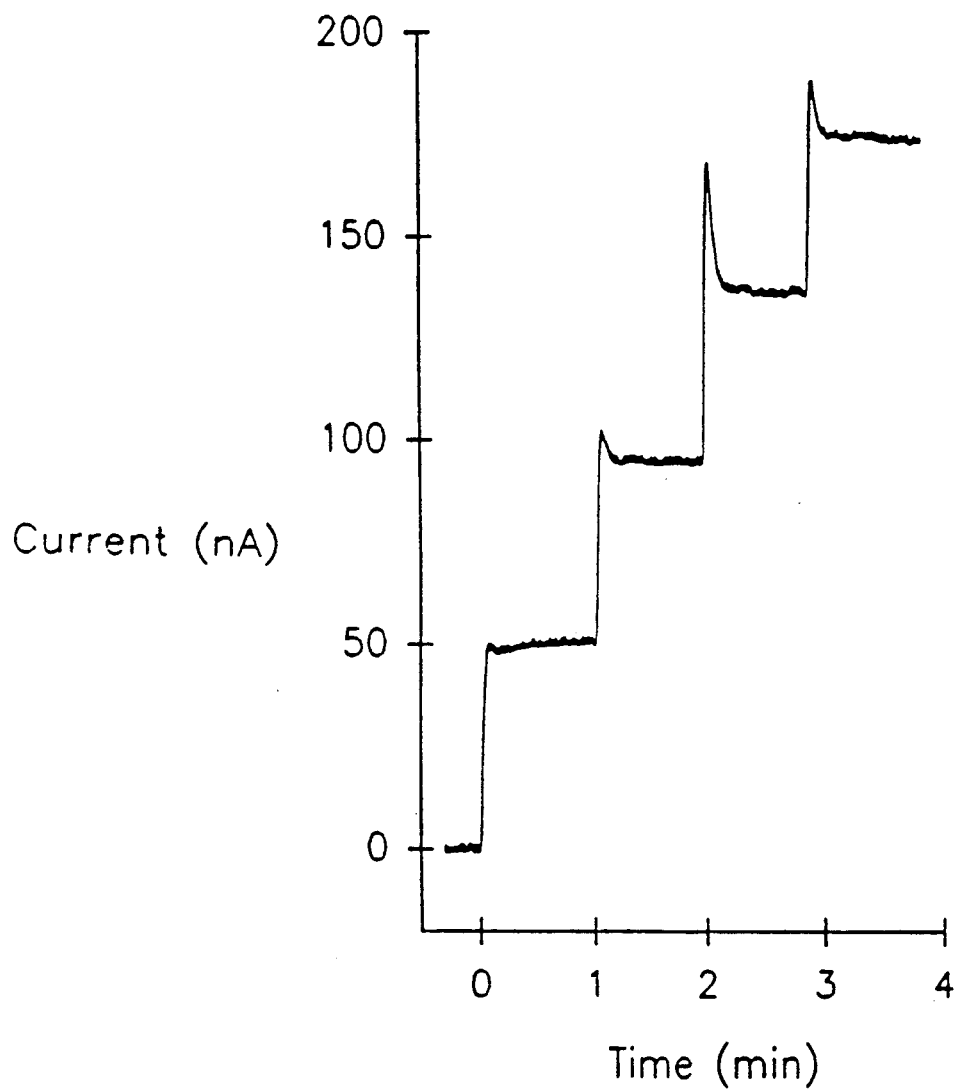
FIG. 8 illustrates the response of a graphite electrode modified with the Meldola Blue modified poly(siloxane) (FIG. 5) to additions of NADH. In this experiment, the applied potential was held at 0 mV vs. SCE, and 0.05 ml aliquots of a 4 mM NADH solution were injected into the constantly stirred test solution (0.1M phosphate buffer solution, pH 7.0, initial volume of 10 ml).
Figure 9:
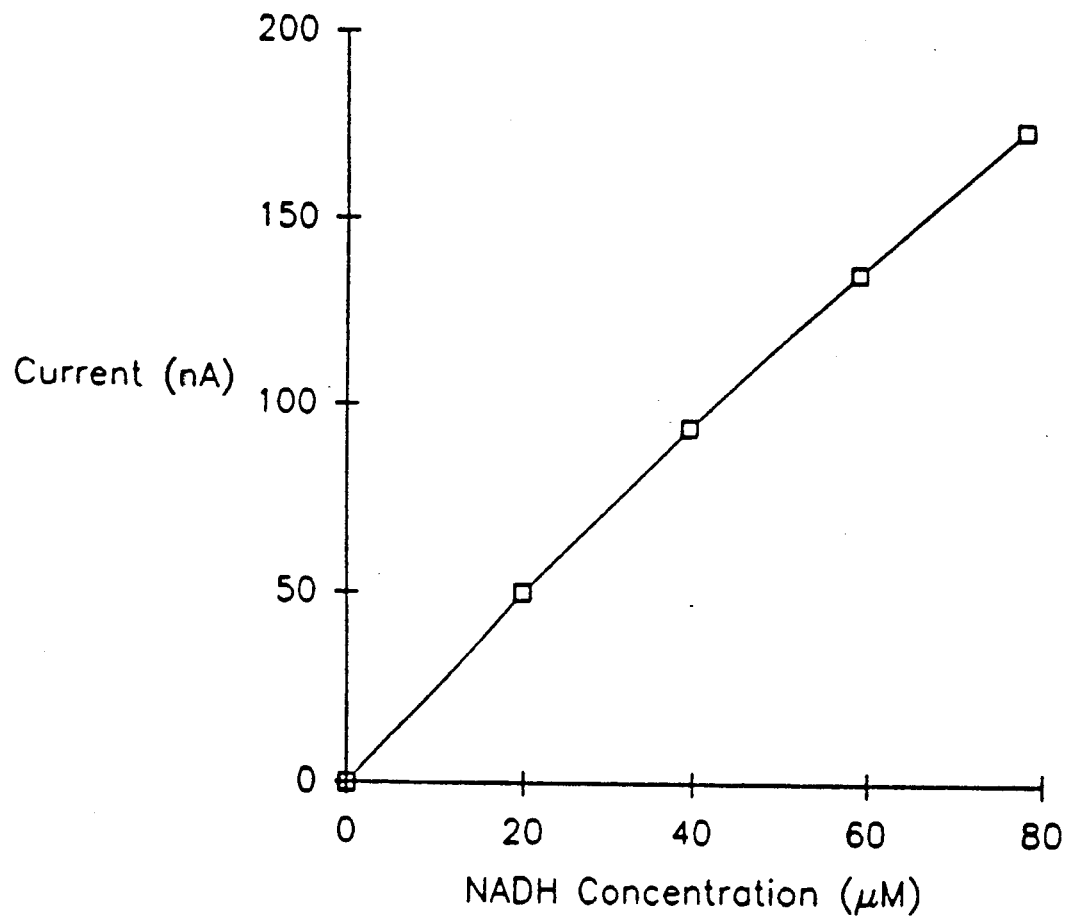
FIG. 9 illustrates a calibration graph for NADH determined from the experimental results shown in FIG. 8.

The polymer-modified electrode described above was also used to reoxidize NADH at a constant potential of 0 mV vs. the SCE reference electrode. The current was measured as a function of the concentration of NADH present in a pH 7.0 phosphate buffer solution with 0.1 M KCl added. As shown in FIG. 8, the current produced upon increasing the NADH concentration from 0 to 20 μM was approximately 50 nA, and the time required for obtaining a steady state response was less than 5 seconds. FIG. 9 shows a NADH calibration plot (steady state current vs. NADH concentration) obtained with the Meldola Blue poly(siloxane)-modified spectrographic graphite electrode at 0 mV vs. SCE.

EXAMPLE 2

Graphite electrode modified with Toluidine Blue O poly(alkane)

Figure 11:
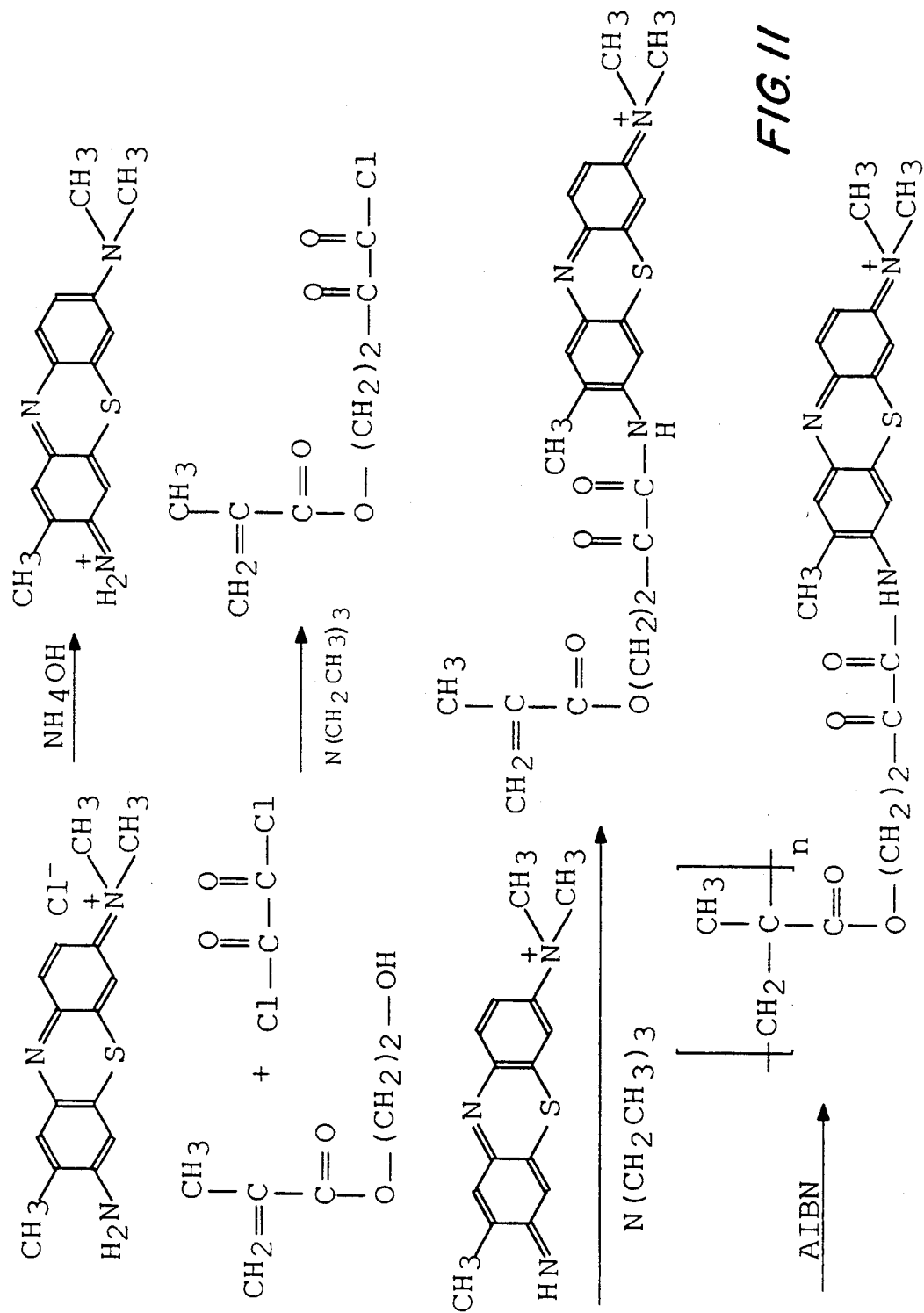
FIG. 11 illustrates the reaction sequence for the synthesis of the Toluidine Blue O-modified poly(alkane) shown in FIG. 10.

The Toluidine Blue O containing poly(alkane) (FIG. 10) was prepared by following the reaction sequence outlined in FIG. 11.

A solution of this redox polymer (1 mg/ml) was made using acetone as the solvent. An amount of 5 μl of this solution was placed onto the surface of a clean, polished spectrographic graphite electrode (electrode diameter: 3.05 mm), and the solvent was allowed to evaporate completely. The resulting polymer-modified electrode was connected to a potentiostat and cyclic voltammetry experiments, as described in EXAMPLE 1, were performed. For these measurements, the reference electrode was a saturated calomel electrode (SCE) and the auxiliary electrode consisted of a platinum wire. The experiments were conducted in 0.1M phosphate buffer solution, pH 7.0, at a sweep rate of 50 mV/s.

Figure 12:
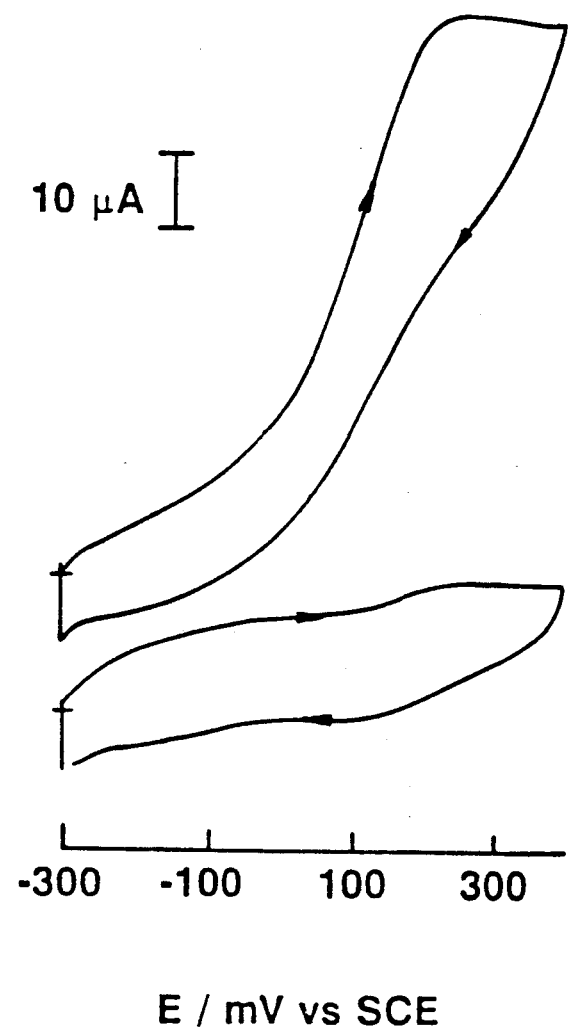
FIG. 12 illustrates cyclic voltammograms with a graphite electrode modified with the Toluidine Blue O modified poly(alkane) (FIG. 10). Voltammogram (a) was measured without NADH in solution, while (b) was measured in the presence of 4 mM NADH. The experiments were conducted in 0.25M phosphate buffer solution, pH 7.5, at a sweep rate of 50 mV/s.

FIG. 12 shows the resulting cyclic voltammograms measured with the graphite electrode modified with the Toluidine Blue O modified poly(alkane). Voltammogram (a) was measured without NADH in solution, and it shows small oxidation and reduction waves corresponding to the electrochemistry of the attached Toluidine Blue O molecules. The formal potential is approximately +200 mV vs. SCE, which agrees well with that measured for the monomeric Toluidine Blue O species (B. Persson and L. Gorton, Journal of Electroanalytical Chemistry, Vol. 292, p. 115 (1990)). Voltammogram (b) in FIG. 12 was measured in the presence of 4 mM NADH. Compared with voltammogram (a), the anodic (oxidation) wave is increased and the cathodic (reduction) wave is decreased. The cyclic voltammograms clearly show the mediating ability of the Toluidine Blue O-containing poly(alkane).

EXAMPLE 3

Alcohol dehydrogenase / NAD+ / Meldola Blue poly(siloxane) / carbon paste electrode In the following embodiment of the present invention, an amperometric biosensor was constructed based on a carbon paste electrode modified with a dehydrogenase, a coenzyme, and a mediating redox polymer. The enzyme used was alcohol dehydrogenase and the polymer was the Meldola Blue modified poly(siloxane) shown in FIG. 5. This electrochemical biosensor is described with reference to one particular measurement, the determination of the ethanol concentration in an aqueous mixture. While the measurement of ethanol concentration is one object of the invention, other and broader objects are not hereby excluded.

Figure 13:
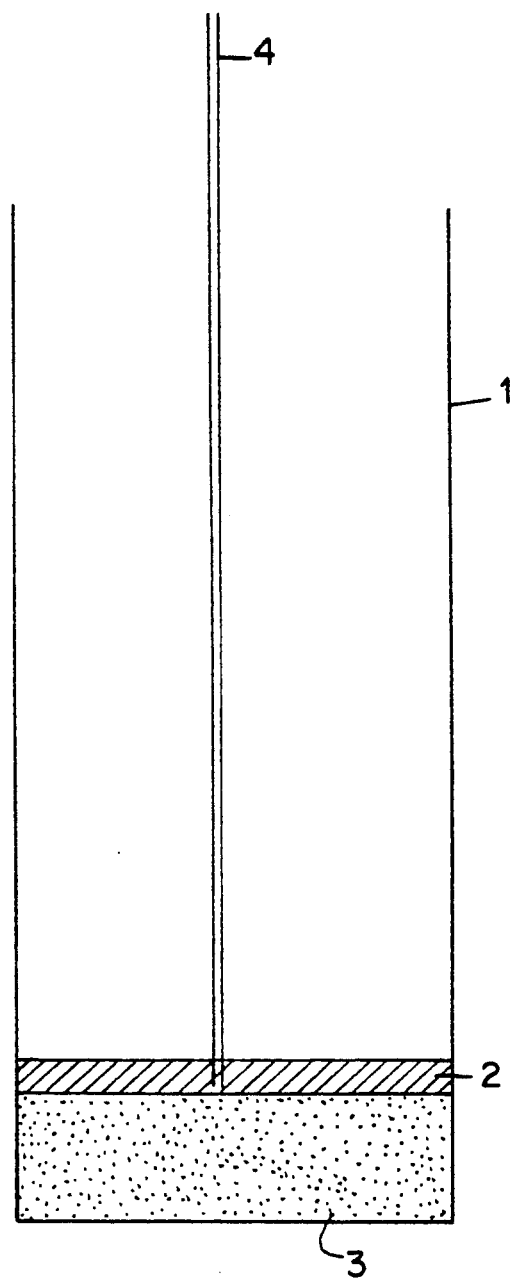
FIG. 13 illustrates the structural details of the enzyme electrode of the present invention. The enzyme electrode comprises a cylindrical electrode holder 1 of an electrically insulating material, an electron collector 2 of carbon formed in a disc-like configuration and mounted recessed in the electrode holder 1, a leading wire 4 connected to the electron collector 2, and a carbon paste 3 containing the enzyme-coenzyme-polymer system.

FIG. 13 shows the structural details of the enzyme electrode of the present invention. The enzyme electrode comprises a cylindrical electrode holder 1 of an electrically insulating material, an electron collector 2 of carbon formed in a disc-like configuration and mounted recessed in the electrode holder 1, a leading wire 4 connected to the electron collector 2, and a carbon paste 3 containing the enzyme-coenzyme-polymer system.

The carbon paste for this biosensor was constructed by thoroughly mixing 50 mg of graphite powder with 6.0 mg of the Meldola Blue containing polymer, the latter being dissolved in acetone. After evaporation of the solvent, 5.0 mg of alcohol dehydrogenase (300 units/mg), 20.0 mg of NAD+, and 20 µl of paraffin oil were added, and the resulting mixture was blended into a paste. The paste was packed into a 1 mm deep recess at the base of a plastic electrode holder (electrode area of 0.020 cm$^2$). For the measurement of the current response, the reference electrode was a saturated calomel electrode (SCE) and the auxiliary electrode consisted of a platinum wire.

The resulting enzyme electrode was connected to a potentiostat and maintained at a constant potential of +100 mV vs. the SCE reference electrode. The current was measured as a function of the concentration of ethanol present in a pH 7.0 phosphate buffer solution with 0.1M KCl added. The current produced upon increasing the ethanol concentration from 0 to 10 mM was 28 nA, and the time required for obtaining 95% of the steady state response was approximately 1 minute.

We claim:

1. A redox polymer-modified electrode for use in liquid mixtures of components for detecting the presence of, or measuring the amount of, one or more selected components by the electrochemical regeneration of coenzymes dihydronicotinamide adenine dinucleotide (NADH), dihydronicotinamide adenine dinucleotide phosphate (NADPH), or analogues thereof, characterized by having an adsorbed redox polymer comprising polysiloxane, polyalkane, poly(ethylene oxide), poly(ethylene imine), or copolymers thereof, which contain covalently attached mediators comprising phenazinium ions, phenazinones, phenoxazinium ions, phenoxazones, phenothiazinium ions, or phenothiazinones, substituted or unsubstituted; an electrode substrate with said polymer on a surface thereof; one or more enzymes, at least one of which is a de-hydrogenase, in dissolved, suspended or immobilized form on or at the electrode surface; and NADH or NADPH coenzymes or analogues thereof dissolved or immobilized in said redox polymer, whereby said coenzyme can be re-oxidized by the electrode.

2. The electrode of claim 1, characterized in that the electrode substrate is selected from the group consisting of gold, silver, platinum, nickel, indiumtin oxide, tin oxide, graphite and conducting carbon.

3. The electrode of claim 1, characterized in that the enzyme or enzymes are retained adjacent to said electrode by a membrane permeable to small molecules.

4. The electrode of claim 1, characterized in that the redox polymer, the NADH or NADPH or analogues thereof, and the enzymes are contained within a graphite paste matrix.

5. The electrode of claim 1, characterized in that one or more enzyme, at least one of which is a de-hydrogenase, have been immobilized in the redox polymer matrix.

6. A method of making an electrode for the electrochemical regeneration of coenzymes dihydronicotinamide adenine dinucleotide (NADH), dihydronicotinamide adenine dinucleotide phosphate (NADPH), or analogues thereof, comprising the steps of: preparing an electrode substrate; depositing a redox polymer film and coenzymes of claim 10 onto said electrode surface from a common organic, aqueous or mixed aqueous-organic solution containing in a dissolved or suspended form redox mediator and said coenzyme; depositing onto said redox polymer film from an aqueous or mixed aqueous-organic solvent a layer of enzymes, at least one of which is a de-hydrogenase, to allow the enzymes to penetrate said redox polymer film.

7. A method of making an electrode according to claim 6, which includes depositing on an outer surface of the electrode a membrane permeable to small molecules.

8. A method of improving the performance of a biochemical fuel cell which operates with de-hydrogenases as catalysts, with coenzyme as the energy-transferring redox couple, and with the electrode of claim 1 as an anode in said fuel cell.

9. A method of analysis in systems utilizing coenzyme-dependent enzyme, employing the electrode of claim 1 in an analytical apparatus in which the coenzymes dihydronicotinamide adenine dinucleotide (NADH), dihydronicotinamide adenine dinucleotide phosphate (NADPH), or analogues thereof are generated.

* * * * *